US011566994B2

(12) United States Patent
Kung et al.

(10) Patent No.: US 11,566,994 B2
(45) Date of Patent: Jan. 31, 2023

(54) DEVICE FOR CONTINUOUS FOCUSING AND ROTATION OF BIOLOGICAL CELLS AND ITS USE FOR HIGH THROUGHPUT ELECTROROTATION FLOW CYTOMETERY

(71) Applicant: The Regents of the University of California, Oakland, CA (US)

(72) Inventors: Yu-Chun Kung, South Pasadena, CA (US); Tianxing Man, Los Angeles, CA (US); Pei-Yu E. Chiou, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 630 days.

(21) Appl. No.: 16/500,382

(22) PCT Filed: Apr. 5, 2018

(86) PCT No.: PCT/US2018/026314
§ 371 (c)(1),
(2) Date: Oct. 2, 2019

(87) PCT Pub. No.: WO2018/187610
PCT Pub. Date: Oct. 11, 2018

(65) Prior Publication Data
US 2020/0386666 A1 Dec. 10, 2020

Related U.S. Application Data

(60) Provisional application No. 62/482,108, filed on Apr. 5, 2017.

(51) Int. Cl.
*G01N 15/14* (2006.01)
*C07K 1/02* (2006.01)
(Continued)

(52) U.S. Cl.
CPC ......... *G01N 15/1425* (2013.01); *C07K 1/026* (2013.01); *G01N 15/147* (2013.01);
(Continued)

(58) Field of Classification Search
None
See application file for complete search history.

(56) References Cited

U.S. PATENT DOCUMENTS

2002/0036142 A1 3/2002 Gascoyne et al.
2002/0123078 A1 9/2002 Seul et al.
(Continued)

OTHER PUBLICATIONS

Arnold, W.M. et al., "Electro-rotation: Development of a Technique for Dielectric Measurements on Individual Cells and Particles", Journal of Electrostatics, 1988, vol. 21, No. 2-3, pp. 151-191.
(Continued)

*Primary Examiner* — Eileen M Adams
(74) *Attorney, Agent, or Firm* — Tom Hunter; Weaver Austin Villeneuve & Sampson LLP

(57) ABSTRACT

In certain embodiments a device is provided for electrorotation flow. In certain embodiments the device comprises a microfluidic channel comprising a plurality of electrodes disposed to provide dielectrophoretic (DEP) forces that are perpendicular to hydrodynamic flows along the channel; and a fluid within the channel providing the hydrodynamic flow along the channel; wherein the device is configured to apply focusing voltages to the electrodes that provide an electric field minimum in the channel and that focus cells, particles, and/or molecules or molecular complexes within the channel; and where the device is configured to apply rotation-inducing voltages to the electrodes that induce rotation of the cells, particles, molecules and/or molecular complexes as they flow through the channel.

19 Claims, 4 Drawing Sheets

(51) Int. Cl.
*G01N 27/00* (2006.01)
*G01N 15/10* (2006.01)

(52) U.S. Cl.
CPC ..... *G01N 15/1459* (2013.01); *G01N 15/1463* (2013.01); *G01N 15/1475* (2013.01); *G01N 27/00* (2013.01); *G01N 2015/1006* (2013.01)

(56) References Cited

U.S. PATENT DOCUMENTS

| | | |
|---|---|---|
| 2002/0166766 A1 | 11/2002 | Seul et al. |
| 2002/0190732 A1 | 12/2002 | Cheng et al. |
| 2003/0022393 A1 | 1/2003 | Seul et al. |
| 2003/0119057 A1* | 6/2003 | Gascoyne .............. B82Y 30/00 435/7.1 |
| 2004/0011651 A1 | 1/2004 | Becker et al. |
| 2004/0129568 A1 | 7/2004 | Seul et al. |
| 2005/0032192 A1 | 2/2005 | Vesey et al. |
| 2005/0114041 A1 | 5/2005 | Gawad et al. |
| 2006/0152708 A1 | 7/2006 | Muller et al. |
| 2008/0067068 A1 | 3/2008 | Li |
| 2008/0070311 A1 | 3/2008 | Li |
| 2008/0312843 A1 | 12/2008 | Esteban et al. |
| 2009/0229980 A1 | 9/2009 | Hughes et al. |
| 2010/0224493 A1 | 9/2010 | Davalos et al. |
| 2010/0282984 A1 | 11/2010 | Kreysing et al. |
| 2012/0085649 A1 | 4/2012 | Sano et al. |
| 2012/0142032 A1 | 6/2012 | Morgan et al. |
| 2013/0083315 A1* | 4/2013 | Lo ..................... G01N 15/1434 356/402 |
| 2014/0339088 A1 | 11/2014 | Schmelz et al. |
| 2014/0341863 A1 | 11/2014 | Marasco et al. |
| 2015/0247820 A1 | 9/2015 | Davalos et al. |
| 2015/0360237 A1 | 12/2015 | Hayes et al. |
| 2017/0028408 A1 | 2/2017 | Menachery et al. |
| 2018/0141048 A1* | 5/2018 | Kung ..................... B03C 5/005 |

OTHER PUBLICATIONS

Benhal, P. et al., "AC Electric Field Induced Dipole-based on-chip 3D Cell Rotation", Royal Society of Chemistry, Lab on a Chip, 2014, vol. 14, No. 15, pp. 2717-2727.

Fuhr, G. et al., "Levitation, Holding, and Rotation of Cells Within Traps Made by High-frequency Fields", Biochimica et Biophysica Acta, 1992, vol. 1108, No. 2, pp. 215-223.

Han, S. et al., "An Electrorotation Technique for Measuring the Dielectric Properties of Cells With Simultaneous Use of Negative Quadrupolar Dielectrophoresis and Electrorotation", Analyst, 2013, vol. 138, No. 5, pp. 1529-1537.

Ino, K. et al., "Electrorotation Chip Consisting of Three-dimensional Interdigitated Array Electrodes", Sensors and Actuators B: Chemical, 2011, vol. 153, No. 2, pp. 468-473.

International Preliminary Report on Patentability dated Oct. 8, 2019 in PCT Application PCT/US2018/026314.

International Search Report & Written Opinion dated Jun. 28, 2018 in PCT Application PCT/US2018/026314.

Jones, Thomas "Basic Theory of Dielectrophoresis and Electrorotation", IEEE Eng Med Biol Mag., 2003, vol. 22, No. 6, pp. 33-42.

Kung, Y.C. et al., "Fabrication of 3D high aspect ratio PDMS microfluidic networks with a hybrid stamp." Lab Chip, 2015, vol. 15, No. 8, pp. 1861-1868.

Kung, Y.C. et al. "Tunnel Dielectrophoresis for Tunable, Single-Stream Cell Focusing in Physiological Buffers in High-Speed Microfluidic Flows." Small, 2016, vol. 12, No. 32, pp. 4343-4348.

Rohani, A, et al., "Electrical Tweezer for Highly Parallelized Electrorotation Measurements Over a Wide Frequency Bandwidth", Electrophoresis, 2014, vol. 35, No. 12-13, pp. 1795-1802.

Wang et al., "Dielectrophoresis switching with vertical sidewall electrodes for microfluidic flow cytometry." Lab Chip., Sep. 2007, vol. 7, No. 9, pp. 1114-1120 [NIH Public Access-Author Manuscript—13 pages].

* cited by examiner

DEVICE FOR CONTINUOUS FOCUSING AND ROTATION OF BIOLOGICAL CELLS AND ITS USE FOR HIGH THROUGHPUT ELECTROROTATION FLOW CYTOMETERY

CROSS-REFERENCE TO RELATED APPLICATIONS

This application is a U.S. 371 National Phase of PCT/US2018/026314, filed on Apr. 5, 2018, which claims priority to and benefit of U.S. Ser. No. 62/482,108, filed on Apr. 5, 2017, both of which are incorporated herein by reference in their entirety for all purposes.

STATEMENT OF GOVERNMENTAL SUPPORT

This invention was made with Government support under DBI1256178, awarded by the National Science Foundation. The Government has certain rights in the invention.

BACKGROUND

Label-free characterization of cells based on their sizes, membrane properties, stiffness, and dielectric properties can be applied for cell identification and disease diagnosis (Jones (2003) *IEEE Eng. Med. Biol. Mag.*, 22(6): 33-42). Electrorotation (ROT) is a useful method for characterizing cells' dielectric properties. The rotation speed of a cell in a rotating electric field is dependent upon the cell's dielectric composition and its relative polarization property to the surrounding medium. Through measuring cells' rotation speeds at different frequencies and in different media, cells' dielectric properties can be extracted (Arnold and Zimmermann (1988) *J. Electrostatics*, 21(2-3): 151-191).

To measure the ROT speed of a cell, four electrodes are typically arranged in a crisscross pattern on a substrate. When a cell is located at the center of these electrodes, four ROT signals with different phase delays are applied to these electrodes. Conventionally, prior to the measurement, a cell needs to be trapped in the center of these electrodes before rotation. Every cell under measurement needs to be positioned at the same location with the same electric field strength for fair comparison. Positioning single cells in a microfluidic device is not trivial and a time-consuming task. In addition, the measurement result is adversely affected by the friction force between the rotating cell and the substrate. Correction of the rotation data is required to extract the dielectric properties of a cell.

Methods have been proposed for caging and levitating single cells above the substrate to avoid the friction problem (Benhal et al. (3025) *Lab on a Chip*, 14(15): 2717-2727; Han et al. (2013) *Analyst*, 138(5): 1529-1537). For example, by using a three-dimensional (3D) octode, in which four crisscross electrodes are patterned on both the top and the bottom substrates, a cell can be trapped in the center between the top and the bottom substrates to avoid the friction issue during rotation. However, the throughput is a major issue. It takes minutes to stabilize the flow, and stably trap a cell in a cage and rotate it to obtain the ROT spectrum, and release it from the cage for the next measurement. Although parallel cages can be patterned to increase the throughput, loading single cells into these cages, imaging them sequentially, releasing them after measurement, and repeating the same procedure for the next measurement is still a time-consuming process (Fuhr et al. (1992) *Biochimica et Biophysica Acta (BBA)—Biomembranes*, 1108(2): 215-223; Ino et al. (2011) *Sensors and Actuators B: Chemical*, 153(2): 468-473; Rohani et al. (2014) *Electrophoresis*, 35(12-13): 1795-1802).

SUMMARY

In various embodiments a novel microfluidic-based high-throughput electrorotation flow cytometer for label-free single-cell (or other particle) analysis in continuous flows is provided. In certain embodiments this is realized by a heterogeneously integrated microfluidic channel with electrodes for high precision 3D single stream focusing and electrorotation of cells in high speed flows. This device provides 4 orders of magnitude higher throughput than prior electrorotation based cytometers.

Various embodiments contemplated herein may include, but need not be limited to, one or more of the following:

Embodiment 1: A device for electrorotation flow cytometry, said device comprising:
a microfluidic channel comprising a plurality of electrodes disposed to provide dielectrophoretic (DEP) forces that are perpendicular to hydrodynamic flows along the channel; and
a fluid within said channel providing said hydrodynamic flow along said channel;
wherein said device is configured to apply focusing voltages to said electrodes that provide an electric field minimum in said channel and that focus cells, particles, and/or molecules or molecular complexes within said channel; and
wherein said device is configured to apply rotation-inducing voltages to said electrodes that induce rotation of said cells, particles, molecules and/or molecular complexes as they flow through said channel.

Embodiment 2: The device of embodiment 1, wherein said device comprises two pairs of electrodes disposed parallel to each other around the microfluidic channel.

Embodiment 3: The device according to any one of embodiments 1-2, wherein said plurality of electrodes comprises electrodes disposed along each side of said microfluidic channel at or near the top of said channel and electrodes disposed along each side of said microfluidic channel at or near the bottom of said channel.

Embodiment 4: The device according to any one of embodiments 1-2, wherein said plurality of electrodes comprises electrodes disposed along the midline of each side of said microfluidic channel and along the midline of the top and bottom of said channel.

Embodiment 5: The device according to any one of embodiments 1-4, wherein said focusing voltages provide negative DEP forces perpendicular to said hydrodynamic flow along said channel.

Embodiment 6: The device according to any one of embodiments 1-5, wherein said focusing voltages applied to said electrodes are ac voltages all having the same frequency.

Embodiment 7: The device according to any one of embodiments 1-6, wherein said rotation-inducing voltages are applied to said electrodes and have phase differences that induces rotation of said cells, particles and/or molecules or molecular complexes.

Embodiment 8: The device of embodiment 7, wherein said rotation-inducing voltages are applied so that neighboring electrodes have a 90 degree phase difference and diagonally opposed electrodes have the same phase.

Embodiment 9: The device according to any one of embodiments 1-8, wherein said rotation-inducing voltages are ac voltages.

Embodiment 10: The device of embodiment 9, wherein said rotation-inducing voltages are at a frequency that is different than the frequency of said focusing voltages.

Embodiment 11: The device according to any one of embodiments 1-10, wherein the amplitude of the rotation-inducing voltages is smaller than the amplitude of the focusing voltages.

Embodiment 12: The device according to any one of embodiments 1-11, wherein said focusing voltages and said rotation-inducing voltages are provided in the same region of said microfluidic channel.

Embodiment 13: The device according to any one of embodiments 1-11, wherein said focusing voltages and said rotation-inducing voltages are provided in different regions of said microfluidic channel.

Embodiment 14: The device according to any one of embodiments 1-13, wherein said rotation-inducing voltages are superimposed on said focusing voltages.

Embodiment 15: The device according to any one of embodiments 1-13, wherein said rotation-inducing voltages are not superimposed on said focusing voltages.

Embodiment 16: The device according to any one of embodiments 1-15, wherein said focusing voltages are independently at a frequency ranging from about 0 Hz, or from about 1 Hz, or from about 100 Hz, or from about 1 kHz, or from about 10 kHz, or from about 50 kHz, or from about 100 kHz, or from about 500 kHz, up to about 5 MHz, or up to about 10 MHz, or up to about 15 MHz, or up to about 20 MHz, or up to about 50 MHz, or up to about 100 MHz, or up to about 500 MHz, or ranging from about 10 kHz, or from about 50 kHz, or from about 100 kHz, or from about 500 kHz, up to about 5 MHz, or up to about 10 MHz, or up to about 15 MHz, or up to about 20 MHz.

Embodiment 17: The device of embodiment 16, wherein said focusing voltages are independently at a frequency ranging from about 15 kHz to about 25 kHz, and/or about 20 kHz.

Embodiment 18: The device according to any one of embodiments 1-17, wherein said focusing voltages independently range from about 0V, or from about 0.001 mV, or from about 0.01 mV, or from about 0.1 mV, or from about 1 mVpp, or from about 100 mVpp, or from about 500 mVpp, or from about 1V, or from about 5 Vpp, or from about 10 Vpp, up to about 500 Vpp, or up to about 100 Vpp, or up to about 80 Vpp, or up to about 50 Vpp, or up to about 40 Vpp, or up to maximum voltage above which a fluid in said channel will undergo electrolysis, or ranges from about 1 Vpp, or from about 5 Vpp, or from about 10 Vpp, up to about 100 Vpp, or up to about 80 Vpp, or up to about 50 Vpp, or up to about 40 Vpp.

Embodiment 19: The device of embodiment 18, wherein said focusing voltages independently range from about 20 Vpp to about 30 Vpp, and/or are about 24 Vpp.

Embodiment 20: The device according to any one of embodiments 1-19, wherein said rotation-inducing voltages are independently at a frequency ranging from about 0 Hz, or from about 1 Hz, or from about 100 Hz, or from about 1 kHz, or from about 10 kHz, or from about 50 kHz, or from about 100 kHz, or from about 500 kHz, up to about 5 MHz, or up to about 10 MHz, or up to about 15 MHz, or up to about 20 MHz, or up to about 50 MHz, or up to about 100 MHz, or up to about 500 MHz, or ranging from about 10 kHz, or from about 50 kHz, or from about 100 kHz, or from about 500 kHz, up to about 5 MHz, or up to about 10 MHz, or up to about 15 MHz, or up to about 20 MHz.

Embodiment 21: The device of embodiment 20, wherein said rotation-inducing voltages are independently at a frequency ranging from about 50 kHz to about 70 kHz, and/or are about 60 kHz.

Embodiment 22: The device according to any one of embodiments 1-21, wherein said rotation-inducing voltages independently range from about 0V, or from about 0.001 mV, or from about 0.01 mV, or from about 0.1 mV, or from about 1 mVpp, or from about 100 mVpp, or from about 500 mVpp, or from about 1 Vpp, or from about 5 Vpp, or from about 10 Vpp, up to about 500 Vpp, or up to about 100 Vpp, or up to about 80 Vpp, or up to about 50 Vpp, or up to about 40 Vpp, or up to maximum voltage above which a fluid in said channel will undergo electrolysis, or ranges from about 1 Vpp, or from about 5 Vpp, or from about 10 Vpp, up to about 100 Vpp, or up to about 80 Vpp, or up to about 50 Vpp, or up to about 40 Vpp.

Embodiment 23: The device of embodiment 22, wherein said rotation inducing voltages independently range from about 10 Vpp to about 30 Vpp, and/or are about 20 Vpp.

Embodiment 24: The device according to any one of embodiments 1-23, wherein said focusing voltages provide a field minimum at the center of said microfluidic channel.

Embodiment 25: The device according to any one of embodiments 1-23, wherein said focusing voltages provide a field minimum at or near one side of said channel.

Embodiment 26: The device according to any one of embodiments 1-23, wherein said focusing voltages provide a field minimum at or near a lower or upper corner (diagonal region) of said channel.

Embodiment 27: The device according to any one of embodiments 1-18, wherein said focusing voltages provide a field minimum at or near one side of said channel.

Embodiment 28: The device according to any one of embodiments 1-27, wherein said microfluidic channel length is at least about 10 µm, or at least about 50 µm, or at least about 100 µm, or at least about 500 µm, or at least about 1 cm, or at least about 2 cm, or at least about 3 cm, or at least about 4 cm, or at least about 5 cm, or at least about 6 cm, or at least about 7 cm, or at least about 8 cm, or at least about 9 cm, or at least about 10 cm, or at least about 25 cm, or at least about 50 cm, or at least about 80 cm, or at least about 100 cm.

Embodiment 29: The device of embodiment 28, wherein said channel is linear.

Embodiment 30: The device according to any one of embodiments 1-29, wherein the average depth of said microfluidic channel ranges from about 0.1 µm, or from about 0.5 µm, or from about 1 µm, or from about 10 µm, or from about 20 µm, or from about 30 µm, up to about 200 µm, or up to about 150 µm, or up to about 100 µm, or up to about 80 µm, or up to about 60 µm, or up to about 50 µm, or up to about 40 µm.

Embodiment 31: The device according to any one of embodiments 1-30, wherein the average width of said microfluidic channel ranges from about 10 µm, or from about 20 µm, or from about 30 µm, or from about 40 µm, or from about 50 µm, or from about 80 µm, or from about 100 µm up to about 500 µm, or up to about 400 µm, or up to about 300 µm, or up to about 200 µm.

Embodiment 32: The device according to any one of embodiments 1-31, wherein said microfluidic channel that has a cross-section ranging from about 50 µm to about 100 µm (width)×about 50 µm to about 100 µm (height), or has a cross-section ranging from about 80 µm to about 100 µm (width)×about 80 µm to about 100 µm (height), or is about 80 µm×83 µm (width×height).

Embodiment 33: The device according to any one of embodiments 1-32, wherein said device perform electrorotation of cells that show weak electrorotation responses in physiological buffers.

Embodiment 34: The device according to any one of embodiments 1-32, wherein said fluid is a buffer.

Embodiment 35: The device according to any one of embodiments 1-34, wherein said fluid has a conductivity ranging from about 0.005 S/m or from about 0.01 S/m up to about 2.0 S/m, or up to about 1.5 S/m, or up to about 1.0 S/m or up to about 0.5 S/m, or up to about 0.2 S/m or up to about 0.1 S/m.

Embodiment 36: The device of embodiment 35, wherein said fluid has a conductivity of about 0.01 S/m.

Embodiment 37: The device of embodiment 34, wherein said fluid comprises a mammalian ringer's solution.

Embodiment 38: The device of embodiment 34, wherein said fluid comprises PBS.

Embodiment 39: The device according to any one of embodiments 1-38, wherein said hydrodynamic flows are at a rate ranging up to about 10 m/s, or up to about 5 m/s, or up to about 1 m/s, or up to about 50 cm/s, or up to about 20 cm/s, or up to about 15 cm/s, or up to about 11 cm/s, or up to about 10 cm/s, or up to about 8 cm/s, or up to about 5 cm/s, or up to about 3 cm/s, or up to about 1 cm/s, or up to about 500 µm/s, or up to about 250 µm/s, or up to about 100 µm/s, or up to about 50 µm/s, or up to about 30 µm/s, or up to about 20 µm/s, or up to about 10 µm/s.

Embodiment 40: The device according to any one of embodiments 1-39, wherein channel is fabricated from a material selected from the group consisting of silicon, a plastic, and an elastomeric material.

Embodiment 41: The device of embodiment 40, wherein said elastomeric material is selected from the group consisting of polydimethylsiloxane (PDMS), polyolefin plastomers (POPs), perfluoropolyethylene (a-PFPE), polyurethane, polyimides, and cross-linked NOVOLAC® (phenol formaldehyde polymer) resin.

Embodiment 42: The device of embodiment 40, wherein said channel is fabricated from PDMS.

Embodiment 43: The device according to any one of embodiments 1-42, wherein said device further comprises a camera configured to capture images of said cells, particles and/or molecules or molecular complexes as they flow through said channel.

Embodiment 44: A method of inducing rotation of a plurality of cells, particles, molecules and/or molecular complexes, said method comprising:
 introducing said cells, particles, molecules and/or molecular complexes into a device according to any one of embodiments 1-43;
 operating said device to provide said focusing voltages to focus said cells, particles, molecules and/or molecular complexes within said channel; and
 operating said device to provide said rotation-inducing voltages to induce rotation of said cells, particles, molecules and/or molecular complexes as they flow through said microfluidic channel.

Embodiment 45: The method of embodiment 44, wherein said flowing comprises flowing said cells, particles, molecules and/or molecular complexes along at least about 100 µm, or at least about 500 µm, or at least about 1 cm, or at least about 2 cm, or at least about 3 cm, or at least about 4 cm, or at least about 5 cm, at least about 10 cm, or at least about 25 cm, or at least about 50 cm, or at least about 80 cm, or at least about 100 cm of said channel.

Embodiment 46: The method according to any one of embodiments 44-45, wherein said flowing comprises flowing said cells, particles, molecules and/or molecular complexes at a rate ranging up to about 10 m/s, or up to about 5 m/s, or up to about 3 m/s, or up to about 1 m/s, or up to about 50 cm/s, or up to about 20 cm/s, or up to about 15 cm/s, or up to about 11 cm/s, or up to about 10 cm/s, or up to about 8 cm/s, or up to about 5 cm/s, or up to about 3 cm/s, or up to about 1 cm/s, or up to about 500 µm/s, or up to about 250 µm/s, or up to about 100 µm/s, or up to about 50 µm/s, or up to about 25 µm/s, or up to about 10 µm/s.

Embodiment 47: The method according to any one of embodiments 44-46, wherein said cells, particles, molecules and/or molecular complexes is a cell.

Embodiment 48: The method of embodiment 47, wherein said cell is a mammalian cell.

Embodiment 49: The method according to any one of embodiments 47-48, wherein said cells are provided at a concentration ranging from about $10^3$ cells/ml, or from about $10^4$ cells/ml, or from about $10^5$ cells/ml up to about $10^8$ cells/ml, or up to about $10^7$ cells/ml, or up to about $10^6$ cells/ml.

Embodiment 50: The method of embodiment 49, wherein said cells are provided at a concentration that ranges from about $10^5$ cells/ml up to about $10^7$ cells/ml or is about $10^6$ cells/ml.

Embodiment 51: The method according to any one of embodiments 44-46, wherein said cells, particles, molecules and/or molecular complexes is a particle.

Embodiment 52: The method according to any one of embodiments 44-46, wherein said cells, particles, molecules and/or molecular complexes is a molecular complex.

Embodiment 53: The method of embodiment 52, wherein said molecular complex is antibody antigen complex or a cell bound by an antibody.

Embodiment 54: The method according to any one of embodiments 44-53, wherein said method comprises detecting rotation of said cells, particles, molecules and/or molecular complexes.

Embodiment 55: The method of embodiment 54, wherein said detecting rotation is by use of a camera.

Embodiment 56: The method according to any one of embodiments 44-55, wherein said method provides a throughput of at least 10, or at least 20, or at least 30, or at least 40 cells, particle, molecules, and/or molecular complexes per second.

Embodiment 57: A method of determining an electrical property of cells, particles, molecules and/or molecular complexes, said method comprising:
 introducing at least one of said cells, particles, molecules and/or molecular complexes into a device according to any one of embodiments 1-43;
 operating said device to provide said focusing voltages to focus said cells, particles, molecules and/or molecular complexes within said channel;
 operating said device to provide said rotation-inducing voltages to induce rotation of said cells, particles, molecules and/or molecular complexes as they flow through said microfluidic channel; and
 measuring the rotation of said at least one of said cell, particle, molecule and/or molecular complex and thereby determining the electrical property of said cell, particle, molecule and/or molecular complex.

Embodiment 58: The method of embodiment 57, wherein said of cells, particles, molecules and/or molecular complexes comprises a moiety selected from the group consisting of a particle, a biological molecule, a biological complex, an immune complex, a liposome, a protoplast, a platelet, a bacterium, a virus, and a prokaryotic cell, and a eukaryotic cell.

Embodiment 59: The method of embodiment 57, wherein said of cells, particles, molecules and/or molecular complexes comprises a cell.

Embodiment 60: The method of embodiment 59, wherein said cell comprise a mammalian cell.

Embodiment 61: The method according to any one of embodiments 57-60, wherein the rotation of said of cells, particles, molecules and/or molecular complexes is measured at more than one rotation-inducing voltage frequency.

Embodiment 62: The method of embodiment 61, wherein the rotation of said of cells, particles, molecules and/or molecular complexes is measured at at least three, or at least 4, or at least 5 different rotation-inducing voltage frequencies.

Embodiment 63: The method according to any one of embodiments 57-62, wherein the electrical properties of a plurality of cells, particles, molecules and/or molecular complexes are measured.

Embodiment 64: The method of embodiment 63, wherein said plurality of cells, particles, molecules and/or molecular complexes are a heterogeneous population.

Embodiment 65: The method of embodiment 63, wherein said plurality of cells, particles, molecules and/or molecular complexes are a homogenous population.

Embodiment 66: The method according to any one of embodiments 57-65, further comprising identifying those cells, particles, molecules and/or molecular complexes that have similar electrical properties.

Embodiment 67: The method according to any one of embodiments 57-66, wherein said electrical property is a dielectric property.

Embodiment 68: The method according to any one of embodiments 57-67, wherein said measuring the rotation is by use of a camera.

Embodiment 69: The method according to any one of embodiments 57-68, wherein said method provides a throughput of at least 10, or at least 20, or at least 30, or at least 40 cells, particle, molecules, and/or molecular complexes per second.

Embodiment 70: A method of identifying an agent that changes the electrorotational properties of a cell, said method comprising:
introducing cells into a device according to any one of embodiments 1-43;
operating said device to provide said focusing voltages to focus said cells within said channel;
operating said device to provide said rotation-inducing voltages to induce rotation of said cells as they flow through said microfluidic channel;
measuring the rotation of said cells;
contacting said cells with a test agent;
operating said device to provide said focusing voltages to focus cells contacted with said test agent within said channel;
operating said device to provide said rotation-inducing voltages to induce rotation of said cells contacted with said test agent as they flow through said microfluidic channel;
comparing the rotation of a cell that was not exposed to said candidate molecule with the rotation of said cell after contact with said candidate molecule; and
identifying said candidate molecule as an agent that changes said electrorotational properties of said cell if said cells contacted with said candidate molecule have different electrorotational properties than said cells not contacted with said test agent.

Embodiment 71: The method of embodiment 70, wherein said test agent is a small organic molecule.

Embodiment 72: The method according to any one of embodiments 70-71, wherein said test agent is a pharmaceutical.

Embodiment 73: The method of embodiment 70, wherein said test agent is a biomolecule.

Embodiment 74: The method of embodiment 73, wherein said biomolecule is selected from the group consisting of a protein, nucleic acid, enzyme, antibody, lipid, sugar, lectin.

Embodiment 75: The method according to any one of embodiments 70-74, wherein said method comprises determining a concentration dependence of said test agent on said electrotational property.

Embodiment 76: The method according to any one of embodiments 70-75, wherein the rotation is measured at more than one frequency.

Embodiment 77: The method according to any one of embodiments 70-76, wherein the rotation of said of cells are measured at more than one rotation-inducing voltage frequency.

Embodiment 78: The method of embodiment 61, wherein the rotation of said of cells, particles, molecules and/or molecular complexes is measured at at least three, or at least 4, or at least 5 different rotation-inducing voltage frequencies.

Embodiment 79: The method according to any one of embodiments 70-78, wherein said cells are a heterogeneous population.

Embodiment 80: The method according to any one of embodiments 70-78, wherein said cells are a homogeneous population.

Embodiment 81: The method according to any one of embodiments 70-80, further comprising identifying those cells that have a similar or the same response to said test agent.

Embodiment 82: The method according to any one of embodiments 70-81, wherein said measuring the rotation is by use of a camera.

Embodiment 83: The method according to any one of embodiments 70-82, wherein said method provides a throughput of at least 10, or at least 20, or at least 30, or at least 40 cells per second.

Embodiment 84: A method of determining the identity or concentration of an analyte in a sample comprising, said method comprising:
introducing said sample into a device according to any one of embodiments 1-43;
introducing particles attached to a detection reagent that binds to said analyte into said device;
operating said device to provide said focusing voltages to focus said particles within said channel;
operating said device to provide said rotation-inducing voltages to induce rotation of said particles as they flow through said microfluidic channel; and
determining the identity or concentration of said molecule in said biological sample by comparing the rotation of said particles contacted with said biological sample with particles that have not been contacted with said biological sample where the difference in rotation of the particles contacted with the sample and the particles not contacted with the sample provides a measure of the identity or concentration of said analyte in said sample.

Embodiment 85: The method of embodiment 84, wherein said sample is a biological sample.

Embodiment 86: The method according to any one of embodiments 84-85, wherein said detection reagent is selected from the group consisting of a dye, an antibody, and a ligand.

Definitions

The term "test agent" refers to an agent that is to be screened in one or more assays described herein (e.g., for ability to alter the electrorotational properties of a cell (e.g., alter dielectric properties of a cell). The agent can be virtually any chemical compound or combination of chemical compounds. It can be provided as a single isolated compound or combination of compounds, or can be a member of a chemical (e.g. combinatorial) library. In certain embodiments, the test agent will be a small organic molecule. In certain embodiments the test agent will be a pharmaceutical.

The term "small organic molecule" refers to a molecule of a size comparable to those organic molecules generally used in pharmaceuticals. The term excludes biological macromolecules (e.g., proteins, nucleic acids, etc.). Illustrative small organic molecules range in size up to about 5000 Da, more preferably up to 2000 Da, and most preferably up to about 1000 Da.

The term "biological sample" refers to sample is a sample of biological tissue, cells, or fluid that, in a healthy and/or pathological state, contains an analyte that is to be detected using the methods and devices described herein. Such samples include, but are not limited to sputum/oral fluid, amniotic fluid, blood, a blood fraction, or fine needle biopsy samples (e.g., surgical biopsy, fine needle biopsy, etc.) urine, peritoneal fluid, pleural fluid, and the like. The sample can be taken from a human subject (e.g., patient), or from any non-human mammal, such as a non-human primate, a canine, a feline, an quine, a lagomorph, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, inactivation of interfering components, the addition of reagents, lysing, etc. If such methods of pretreatment are employed with respect to the sample, such pretreatment methods are typically such that the analyte of interest remains in the test sample, preferably at a concentration proportional to that in an untreated test sample (e.g., namely, a sample that is not subjected to any such pretreatment method(s)). Such "treated" or "processed" samples are still considered to be biological samples with respect to the methods described herein.

DETAILED DESCRIPTION

Figure 1:
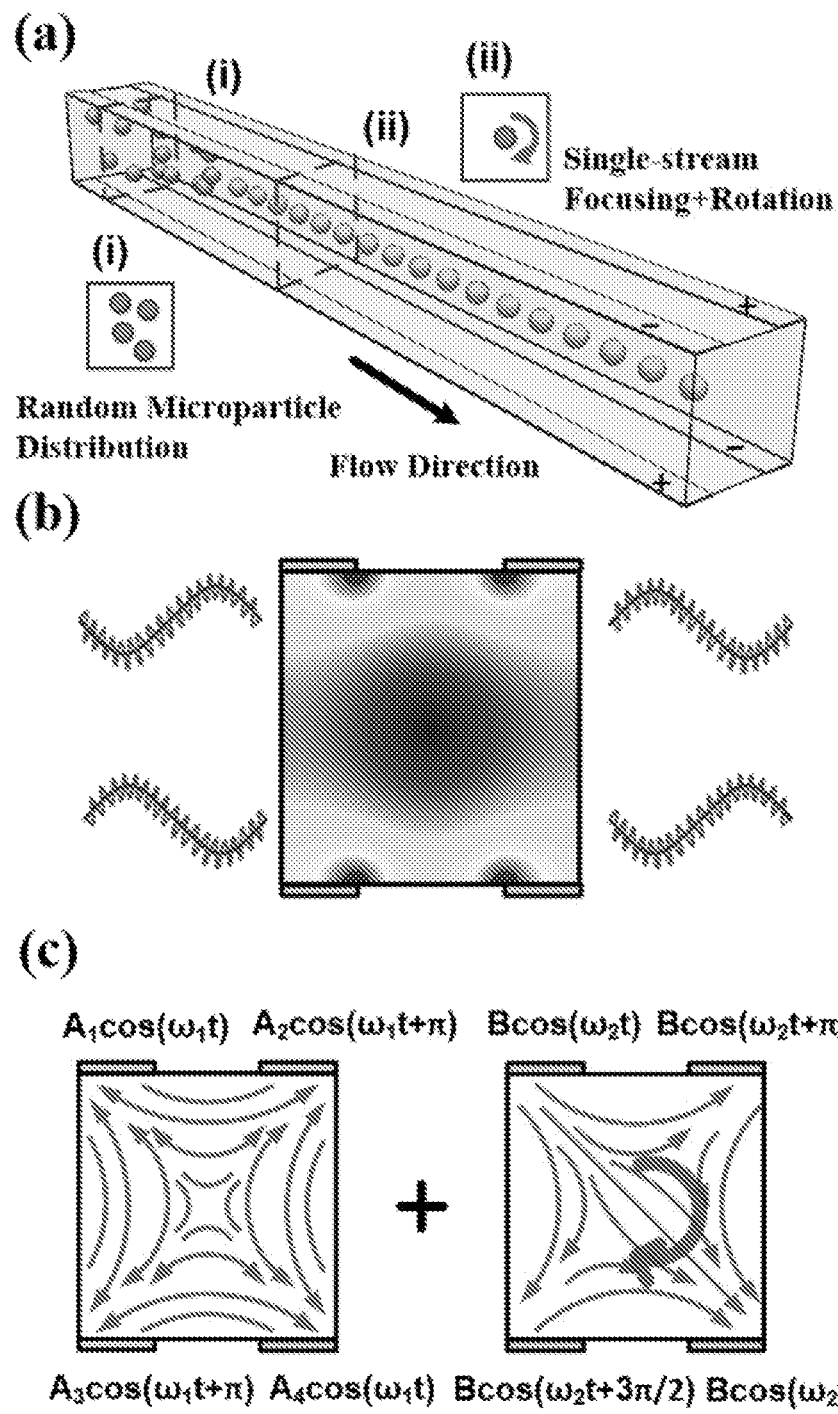
FIG. 1, panels a-c, shows a schematic of a TROT device. (a) Quadro-electrodes are longitudinally aligned with a microchannel to focus randomly distributed cells into a single stream as well as rotating them along the high-speed flow. (b) The cross-section view of the simulated electrical field distribution of the 80 μm×83 μm (width×height) microfluidic channel. Different a.c. signals are applied to the four corner electrodes to focus randomly distributed cells into a single stream. In addition, four rotation signals with different phase delays are superimposed on the focusing signals to simultaneously rotate every cell in the channel. (c) Illustration of the electric field lines of the superimposed focusing (c-i) and rotation (c-ii) signals.

In various embodiments devices are provided to induce and measure electrorotation. Additionally methods utilizing such electrorotation (e.g., electrorotation flow cytometry) are provided. Electrorotation can be used to characterize the behavior or identity of a molecule, cell, or particle. Electrorotation analyses typically involve observing the behavior of molecules, cells, particles, and/or complexes of these materials in an electric field that is applied so as to cause a rotation of the studied material. "Electrorotation" is a term of art that refers to the rotation of a material in an electric field. When a material is subjected to a rotating field, it becomes electrically polarized and the induced polarizations interact with the applied rotating fields, which produces a rotating torque that drives the rotation of the material. The rotation behavior (e.g., rotation rate and direction) depends on the frequency of the rotating field and electrical properties that are specific for the material/particle/cell being rotated. The measurement of rotational behavior can be expressed as a function of the frequency of the applied rotating field. From these measurements, the electrical properties (e.g., electrical conductivity and permittivity) unique to the material can be derived.

The devices described and illustrated herein exploit a novel continuous flow based electrorotation mechanism (referred to herein as tunnel electrorotation (TROT)) that can solve both the friction and the throughput issues encountered by prior electrorotation systems and realize a high throughput electrorotation based flow cytometer for label-free analysis of single cells or other moieties (e.g., cells, organelles, viruses, particles, molecules, molecular complexes, etc.).

The devices described herein exploits dielectrophoresis mechanisms related to dielectrophoresis (DEP). DEP is a phenomenon in which a particle in a non-uniform electric field experiences an electrostatic force moving it towards a stronger electric field region if it is more polarizable than the medium (positive DEP or pDEP), or to a weaker electric field region if the particle is less polarizable than the medium (negative DEP, nDEP). To generate a DEP force on a particle, a spatial electric field intensity gradient is necessary. ROT is a phenomenon in which a particle rotates in a rotating electric field. The physical origin of ROT comes from the phase delay between the induced electric dipole on the particle and the external rotating field. This delay creates an angle between the induced dipole and the external field, and results in a mechanical torque on the particle for rotation. What determines the direction and the magnitude of the torque on a particle, in addition to the electric field strength and frequency, is the dielectric composition of the particles including its materials and structures. DEP and ROT have similar physical origins, both based on the interactions between the field-induced dipole on a particle and their relationship with the external field.

FIG. 1, panel (a), shows the schematic of a TROT device. The quadro-shaped electrodes along the entire channel provide a tunnel-shaped electric field distribution for tunable, sheathless, and three dimensional single-stream cell focusing in high-speed flows (Kung et al. (2015) *Lab Chip,* 15(8): 1861-1868). Electrodes on the top and bottom substrates are laid out and aligned with a straight microfluidic channel to provide negative DEP forces completely perpendicular to the hydrodynamic flow along the entire channel. Single-stream cell focusing is achieved by applying a combination of a.c. voltages ($A_1, A_2, A_3$, and $A_4$) with the same frequency ($\omega_1$) to the four corner electrodes to create an electric field minimum (the dark spot in FIG. 1, panel (b)) in the channel cross section (FIG. 1, panel (c)-i)). Because cell focusing is achieved by negative DEP, randomly distributed cells in the inlet (FIG. 1, panel (a)-i)) migrate to the electric field minimum to achieve single-stream focusing.

To rotate the focused cells, a different set of electrical signals at a different frequency ($\omega_2$) is applied and superimposed on the electrodes. These signals have a phase difference (e.g., a 90-degree phase difference) to their neighboring electrodes (FIG. 1, panel (c)-ii)). The rotation axis of cells is along the channel. The amplitude of rotation signals (B in FIG. 1, panel (c)-ii)) is usually smaller than the focusing signals ($A_1, A_2, A_3$, and $A_4$), and can be adjusted to control the cell rotation speed. FIG. 1, panel (b) shows the superimposed signal configuration on each electrode and the simulated electrical field distribution in the 80 μm×83 μm (width×height) channel cross section.

In various embodiments a camera (e.g., a high-speed camera) can be utilized to capture images of rotating cells continuously. Post-processing and analysis of the captured images can give the information of size, texture, shape, and rotation speed of each individual cell.

It will be recognized that the methods described herein are not simply for use with cells, but can be utilized with essentially any moiety that it is desired analyze and/or manipulate via electrorotation. Such moieties include, but are not limited to cells, organelles, viruses, particles, molecules, molecular complexes, and the like.

Accordingly in certain embodiments a device for electrorotation flow cytometry is provided where the device comprise a a microfluidic channel comprising a plurality of electrodes disposed to provide dielectrophoretic (DEP) forces that are perpendicular to hydrodynamic flows along the channel; and a fluid within said channel providing the hydrodynamic flow along the channel, where the device is configured to apply focusing voltages to the electrodes that provide an electric field minimum in the channel and that focus cells, organelles, viruses, particles, or molecules, or molecular complexes within the channel; and where the device is configured to apply rotation-inducing voltages to the electrodes that induce rotation of the cells, organelles, viruses, particles, or molecules, or molecular complexes as they flow through the channel.

In certain embodiments the device comprises two pairs of electrodes disposed parallel to each other around the microfluidic channel. In certain embodiments the plurality of electrodes comprises electrodes disposed along each side of the microfluidic channel at or near the top of the channel and electrodes disposed along each side of the microfluidic channel at or near the bottom of said channel. In certain embodiments the plurality of electrodes comprises electrodes disposed along the midline of each side of the microfluidic channel and along the midline of the top and bottom of the channel.

In certain embodiments the device is device is configured to apply focusing voltages independently to each of the electrodes and/or to apply rotation voltages independently to each of the electrodes.

In certain embodiments the device is configured to provide, and/or applies focusing voltages that provide negative DEP forces perpendicular to the hydrodynamic flow along the channel. In certain embodiments the device is configured to provide, and/or applies focusing voltages independently to the electrodes where the focusing voltages are ac voltages all having the same frequency. In certain embodiments the device is configured to provide, and/or applies rotation-inducing voltages independently to the electrodes where the focusing voltages have phase differences that induce rotation of moieties (e.g., cells, organelles, viruses, particles, molecules, molecular complexes, etc.) in the microfluidic channel. In certain embodiments the device is configured to provide, and/or applies rotation-inducing voltages so that neighboring electrodes have a 90 degree phase difference and diagonally opposed electrodes have the same phase.

In certain embodiments the device the focusing voltages and/or the rotation-inducing voltages comprise an a.c. voltage. In certain embodiments the focusing voltage(s) and/or rotation voltage(s) are applied to one or more electrodes, or to two or more electrodes, or to three or more electrodes, or to all of the electrodes. In certain embodiments the rotation-inducing voltages are at a frequency that is different than the frequency of the focusing voltages. In certain embodiments the amplitude of the rotation-inducing voltages is smaller than the amplitude of the focusing voltages. In certain embodiments the focusing voltages and said rotation-inducing voltages are provided in the same region of said microfluidic channel. In certain embodiments the focusing voltages and said rotation-inducing voltages are provided in different regions of said microfluidic channel. In certain embodiments the rotation-inducing voltages are superimposed on the focusing voltages. In certain embodiments the rotation-inducing voltages are not superimposed on said focusing voltages.

In certain embodiments the device is configured to provide the voltages described above by integration of a voltage source (e.g., one or more power supplies). In certain embodiments the device is configured to provide the voltages described above by integration of voltage regulators that can adjust one or more externally applied voltages. In certain embodiments the device is configured to provide the voltages described above by electrical coupling to one or more external voltage sources (e.g., power supplies).

In certain embodiments the device is configured to apply to the electrodes focusing voltages and/or the device applies focusing voltages to the electrodes where the focusing voltages are independently applied to the electrodes and are at a frequency ranging from about 0 Hz, or from about 1 Hz, or from about 100 Hz, or from about 1 kHz, or from about 10 kHz, or from about 50 kHz, or from about 100 kHz, or from about 500 kHz, up to about 5 MHz, or up to about 10 MHz, or up to about 15 MHz, or up to about 20 MHz, or up to about 50 MHz, or up to about 100 MHz, or up to about 500 MHz, or ranging from about 10 kHz, or from about 50 kHz, or from about 100 kHz, or from about 500 kHz, up to about 5 MHz, or up to about 10 MHz, or up to about 15 MHz, or up to about 20 MHz.

In certain embodiments the device is configured to apply to the electrodes focusing voltages and/or the device applies focusing voltages to the electrodes independently at a frequency ranging from about 15 kHz to about 25 kHz, and/or about 20 kHz.

In certain embodiments the device is configured to apply to the electrodes focusing voltages and/or the device applies focusing voltages to the electrodes where the focusing voltages independently range from about 0V, or from about 0.001 mV, or from about 0.01 mV, or from about 0.1 mV, or from about 1 mVpp, or from about 100 mVpp, or from about 500 mVpp, or from about 1V, or from about 5 Vpp, or from about 10 Vpp, up to about 500 Vpp, or up to about 100 Vpp, or up to about 80 Vpp, or up to about 50 Vpp, or up to about 40 Vpp, or up to maximum voltage above which a fluid in said channel will undergo electrolysis, or ranges from about 1 Vpp, or from about 5 Vpp, or from about 10 Vpp, up to about 100 Vpp, or up to about 80 Vpp, or up to about 50 Vpp, or up to about 40 Vpp.

In certain embodiments the device is configured to apply to the electrodes focusing voltages and/or the device applies focusing voltages to the electrodes where the focusing voltages independently range from about 20 Vpp to about 30 Vpp, and/or are about 24 Vpp.

In certain embodiments the device is configured to apply to the electrodes rotation-inducing voltages and/or the device applies rotation-inducing voltages to the electrodes where the rotation-inducing voltages are independently applied to the electrodes and are at a frequency ranging from about 0 Hz, or from about 1 Hz, or from about 100 Hz, or from about 1 kHz, or from about 10 kHz, or from about 50 kHz, or from about 100 kHz, or from about 500 kHz, up to about 5 MHz, or up to about 10 MHz, or up to about 15 MHz, or up to about 20 MHz, or up to about 50 MHz, or up to about 100 MHz, or up to about 500 MHz, or ranging from about 10 kHz, or from about 50 kHz, or from about 100 kHz, or from about 500 kHz, up to about 5 MHz, or up to about 10 MHz, or up to about 15 MHz, or up to about 20 MHz.

In certain embodiments the device is configured to apply to the electrodes rotation-inducing voltages and/or the device applies rotation-inducing voltages independently at a frequency ranging from about 50 kHz to about 70 kHz, and/or are about 60 kHz.

In certain embodiments the device is configured to apply to the electrodes rotation-inducing voltages and/or the device applies rotation-inducing voltages to the electrodes where the rotation-inducing voltages independently range from about 0V, or from about 0.001 mV, or from about 0.01 mV, or from about 0.1 mV, or from about 1 mVpp, or from about 100 mVpp, or from about 500 mVpp, or from about 1V, or from about 5 Vpp, or from about 10 Vpp, up to about 500 Vpp, or up to about 100 Vpp, or up to about 80 Vpp, or up to about 50 Vpp, or up to about 40 Vpp, or up to maximum voltage above which a fluid in said channel will undergo electrolysis, or ranges from about 1 Vpp, or from about 5 Vpp, or from about 10 Vpp, up to about 100 Vpp, or up to about 80 Vpp, or up to about 50 Vpp, or up to about 40 Vpp.

In certain embodiments the device is configured to apply to the electrodes rotation-inducing voltages and/or the device applies rotation-inducing voltages to the electrodes where the rotation inducing voltages independently range from about 10 Vpp to about 30 Vpp, and/or are about 20 Vpp.

In certain embodiments the electrodes are configured (e.g., the focusing voltages applied to the electrodes are selected) to provide a field minimum at or near a lower or upper corner (diagonal region) of the channel. In certain embodiments the electrodes are configured (e.g., the focusing voltages applied to the electrodes are selected) to provide a field minimum at or near one side or near the top or bottom of the channel.

In certain embodiments the microfluidic channel length is at least about 1 μm, or at least about 10 μm, or at least about 100 μm, or at least about 500 μm, or at least about 1 cm, or at least about 2 cm, or at least about 3 cm, or at least about 4 cm, or at least about 5 cm, or at least about 6 cm, or at least about 7 cm, or at least about 8 cm, or at least about 9 cm, or at least about 10 cm, or at least about 25 cm, or at least about 50 cm, or at least about 80 cm, or at least about 100 cm.

In certain embodiments the wherein the average depth of the microfluidic channel ranges from about 0.1 μm, or from about 0.5 μm, or from about 1 μm, or from about 10 μm, or from about 20 μm, or from about 30 μm, up to about 100 μm, or up to about 80 μm, or up to about 60 μm, or up to about 50 μm, or up to about 40 μm. In certain embodiments the average width of said microfluidic channel ranges from about 0.1 μm, or from about 0.5 μm, or from about 1 μm, or from about 10 μm, or from about 20 μm, or from about 30 μm, or from about 40 μm, or from about 50 μm, or from about 80 μm, or from about 100 μm up to about 500 μm, or up to about 400 μm, or up to about 300 μm, or up to about 200 μm, or up to about 400 μm, or up to about 500 μm, or up to about 1 mm.

In certain embodiments the microfluidic channel has a cross-section ranging from about 50 μm to about 100 μm (width)× about 50 μm to about 100 μm (height), or has a cross-section ranging from about 80 μm to about 100 μm (width)× about 80 μm to about 100 μm (height), or is about 80 μm×83 μm (width×height).

In certain embodiments the fluid in the microfluidic channel is a low ionic buffer. In certain embodiments the buffer has a conductivity ranging from about 0.005 S/m or from about 0.01 S/m up to about 1.0 S/m or up to about 0.5 S/m, or up to about 0.2 S/m or up to about 0.1 S/m. In certain embodiments the buffer has a conductivity of about 0.01 S/m. In certain embodiments the buffer comprises a mammalian ringer's solution. In certain embodiments the buffer comprises PBS.

In certain embodiments the fluid in the microfluidic channel flows at a rate ranging up to about 10 m/s, or up to about 5 m/s, or up to about 1 m/s, or up to about 50 cm/s, or up to about 20 cm/s, or up to about 15 cm/s, or up to about 11 cm/s, or up to about 10 cm/s, or up to about 8 cm/s, or up to about 5 cm/s, or up to about 3 cm/s, or up to about 1 cm/s, or up to about 500 μm/s, or up to about 250 μm/s, or up to about 100 μm/s, or up to about 50 μm/s, or up to about 30 μm/s, or up to about 20 μm/s, or up to about 10 μm/s.

While the electrorotation devices described herein are illustrated with a single microfluidic channel, it will be recognized that in various embodiments devices comprising a plurality of microfluidic channels can be provided providing "parallel processing" and thereby increase the throughput and/or number of different analytes that can be measured simultaneously. In certain embodiments the devices comprise at least 2, or at least 3, or at least 4, or at least 5, or at least 6, or at least 7, or at least 8, or at least 9, or at least 10 microfluidic channels.

Device Fabrication

Figure 2:
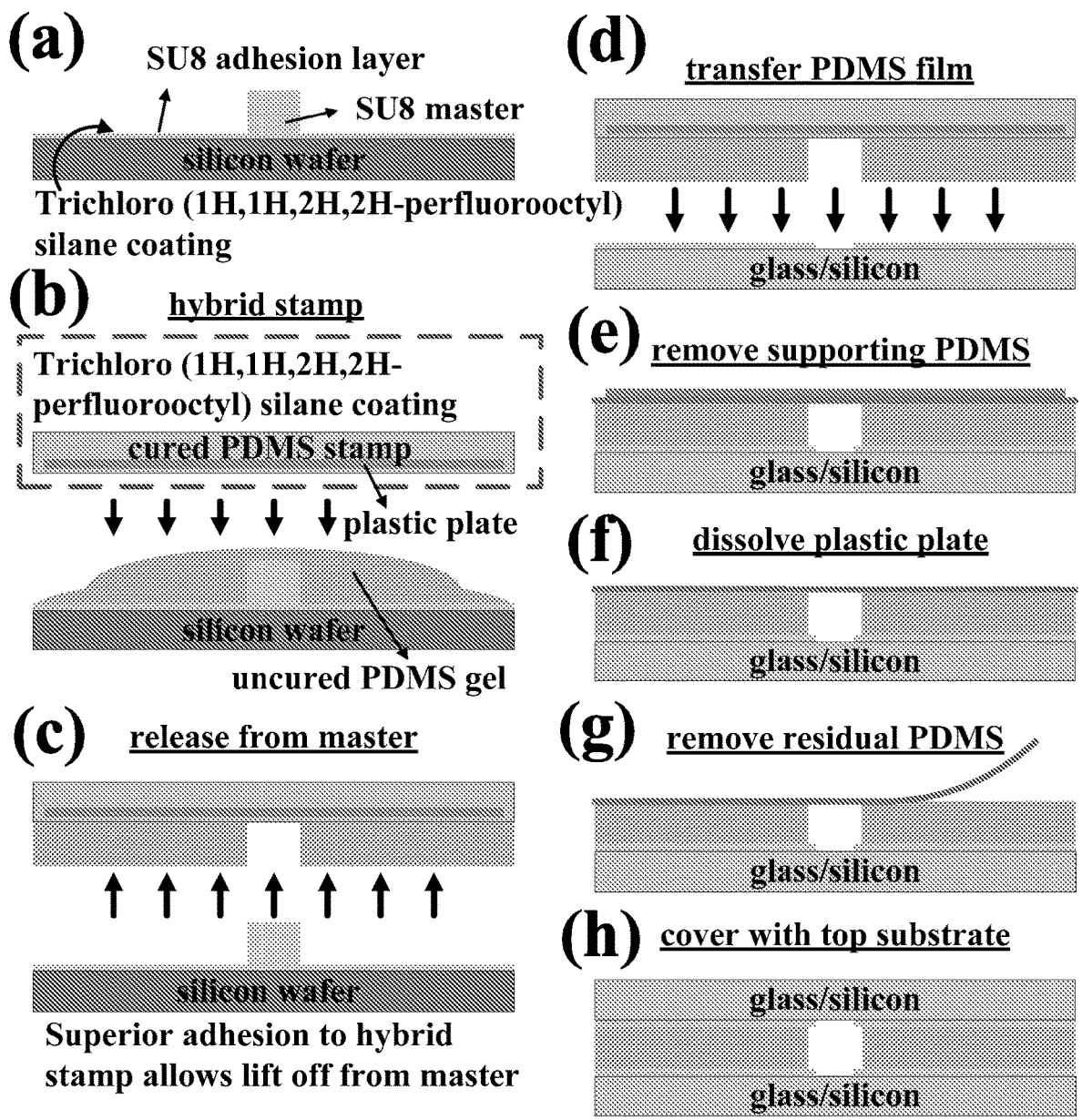
FIG. 2, panels a-h, shows a schematic of the fabrication process flow. (a) A SU-8 master is treated with PFOCTS to facilitate later demolding. (b) Uncured PDMS mixture is poured on the master, and pressed against the hybrid stamp. (c) Due to less PFOCTS treatment on the hybrid stamp compared to the master, the casted PDMS film tends to adhere to the hybrid stamp and allows to be peeled off from the master. (d) Film transferred and alignment bonding is achieved through oxygen plasma treatment. (e) Remove the support PDMS on the hybrid stamp. (f) Dissolve the polystyrene plastic plate in acetone. (g) Remove the residual PDMS thin film to complete the removal of a hybrid stamp. (h) Align and bond the device with a coverslip with strip electrodes to complete the fabrication process by oxygen plasma treatment.

One illustrative, but non-limiting method of fabricating the devices contemplated herein is described and exemplified in Example 1. FIG. 2 shows an illustrative schematic of the microfabrication process flow of a TROT device (Kung et al. (2015) *Lab Chip*, 15(8): 1861-1868). As shown in the figure, it starts from fabricating a SU-8 mold master on a silicon wafer using photolithography (FIG. 2 panel (a)). The master is surface treated with trichloro (1H,1H,2H,2H-perfluorooctyl) silane (97%, Sigma-Aldrich, USA), also called PFOCTS, to facilitate later demolding. Step 2 is to fabricate a hybrid stamp. It starts from preparing the Sylgard 184 silicone elastomer mixture (Dow Corning Corporation, Miland, USA). The weight ratio of Base:Curing agent is 10:1. A few drops of this mixture are poured into a petri dish. A suitable size of polystyrene plastic plate is cut and pressed against the bottom of the petri dish under a pressure of, e.g., 3 psi. A thin layer of polydimethylsiloxane (PDMS) with a thickness of roughly 30 μm is formed between the petri dish and the plastic plate. Additional uncured PDMS is poured to fill up the petri dish, and followed by a curing step at 600° C. in an oven for 12 hours. A hybrid stamp is formed when the plastic plate together with a thin PDMS layer on its surface is peeled off from the petri dish (FIG. 2 panel (b)). The hybrid stamp is also surface treated with PFOCTS for 6 hours.

To fabricate a PDMS thin film with through-layer structures, uncured PDMS is poured onto the SU-8 master mold, pressed by the hybrid stamp under a pressure of 4 psi, and cured at 50° C. in an oven for an hour. Demolding PDMS films from the master mold. During the demolding process, the cured PDMS thin film has stronger adhesion to the hybrid stamp than the master mold since more PFOCTS is coated on the master mold due to a longer treatment time (FIG. 2 panel (c)). To transfer the PDMS thin film, oxygen plasma treatment is performed on both the PDMS thin film on the hybrid stamp and the substrate with strip electrodes to be bonded. The alignment between the channel and strip electrodes is needed (FIG. 2 panel (d)). To remove the hybrid stamp, it starts from peeling off the bulk PDMS part on the plastic plate (FIG. 2 panel (e)), and then dissolving the polystyrene plastic plate in an acetone bath for 4 hours (FIG. 2 panel (f)). This leaves a thin residual PDMS film on the substrate that can be easily peeled off from the device due to prior PFOCTS treatment (FIG. 2 panel (g)) to finish the transfer. This mechanically gentle releasing technique allows us to transfer PDMS thin film with fragile substrates, such as a high aspect ratio vertical wall. Finally, a top coverslip with strip electrodes are aligned and bonded to form a heterogeneously integrated 3D microfluidic TROT device (FIG. 2 panel (h)).

It will be recognized that this fabrication method is illustrative and not limiting. Using the teaching provided herein numerous other fabrication methods will be available to one of skill in the art.

Application of the Electrorotation Devices

In certain embodiments methods for high-throughput analysis of the electrorotation properties of a variety moieties using the devices described herein are provided. Thus, for example, the electrical properties of a plurality of moieties (e.g., cells that may or may not be attached with an antibody, ligand, or other molecule) can be rapidly determined using the devices described herein. In one approach, a plurality of moieties (e.g., cells, organelles, viruses, particles, molecules, or molecular complexes, and the like) are introduced into a device described herein and the device is operated to provide focusing voltages to focus the moieties within the channel; and the device is operated to provide rotation-inducing voltages to induce rotation of the moieties as they flow through the microfluidic channel. In this manner, electrical properties of the moieties can be determined. Although the rotational behavior of the moieties can be measured at a single frequency, desirably in certain embodiments, the rotational behaviors of the moieties are measured at multiple frequencies, e.g., over a particular frequency range. Because the devices described herein provide high throughput rates and multiple devices can be operated in parallel, a high-throughput analysis of many moieties with varying properties can be provided.

Many different types of particles and biological events can be analyzed using the devices and methods described herein. For example, the electrical properties of moieties, including but not limited to, cells, organelles, biological molecules, biological complexes, immune complexes, liposomes, protoplasts, platelets, virus, and the like can be determined using the methods and devices described herein. In certain embodiments the size (e.g., the length of the longest axis) of the moieties analyzed ranges from about 0.05 μm to approximately 100 μm. That is, in certain embodiments, the length of the longest axis of the moiety can be less than or equal to 0.1 μm, 1 μm, 5 μm, 7 μm, 10 μm, 12 μm, 15 μm, 20 μm, 25 μm, 35 μm, 40 μm, 45 μm, 50 μm, 55 μm, 60 μm, 65 μm, 70 μm, 75 μm, 80 μm, 85 μm, 90 μm, 100 μm, 200 μm and 300 μm.

Depending on the specific electrorotation assay application, moieties to be assayed are placed or suspended into aqueous or non-aqueous solutions. In certain embodiments the solutions can be chosen properly in terms of their electrical properties (electrical conductivity and dielectric permittivity) so as to maximize the difference in electrical properties between the moieties and their suspending solutions and to obtain largest electrorotation responses. If viable cells are being analyzed, the suspension solutions can be optimized so as to maintain viability, and if needed, the normal growth of the cells. Maintaining cell growth can involve not only a special growth medium but may also require gaseous molecules to be dissolved in the medium. In certain embodiments to accommodate these applications, the devices described herein can be be fabricated from gas-permeable materials such as porous ceramics or porous silicon (silicon may be selectively etched to some extent), that allow the exchange of the gaseous molecules between the medium (fluid) in the microfluidic channel and its surroundings.

In some embodiments, the electrical properties of the moieties are analyzed by taking electrorotation measurements directly on the moieties themselves, while in other embodiments, the electrical properties of the moieties are analyzed indirectly by monitoring the electrorotational behavior of microbeads, or other markers, that have been attached to the moiety of interest. In some cases, in particular when small particles are under analysis, it is advantageous to use an indirect approach so as to increase the sensitivity of the assay. In certain embodiments such an indirect approach can involve using a marker, such as a dye, antibody, bead, carrier, or other ligand, that is more easily analyzed/detected than the moiety itself. In some cases, electrorotation measurements are made on the markers themselves and in others the marker, when associated with the moiety, perturbs the electrical properties of the particle such that analysis of the moiety itself is facilitated.

One indirect approach, for example, involves the use of an antibody coated bead. In one illustrative, but non-limiting embodiment, to make the antibody coated beads, beads or a resin (e.g., polystyrene microparticles of, e.g., 6 µm diameter approximately $1 \times 10^8$ beads/500 µl) are resuspended in a suitable buffer (e.g., phosphate buffered saline) and are contacted with an equal volume of antibody solution (e.g., approximately 100 µg/ml). The beads and antibody solution are placed on a rocker at 4° C. and are rocked over night. Subsequently, 500 µl of a blocking protein (e.g., 1.0% BSA) and 500 µl of a blocking RNA (e.g., tRNA), which are used to block the sites of non-specific binding on the beads, are added. In certain embodiments the blocking reaction can also carried out at 4° C. for approximately 2 hours. The resulting antibody coated beads have a large quantity of antibody bound to the bead and these beads can be used to interact with a moiety to be analyzed.

Next, the antibody coated beads can be contacted with a moiety that is bound by the antibody and the bead/antibody/moiety complexes are introduced into the microfluidic channel(s) in the devices described herein. Electrorotation measurements are taken on beads that are complexed with the particle. As a control, electrorotation measurements on antibody-coated beads that are not contacted with a particle can be made. In certain embodiments electrorotation measurements are made on the same beads before contact with the moiety. By comparing the values obtained from the electrorotation measurements of the beads before and after contact with the particle, one of skill can indirectly determine the electrical properties of very small particles including peptides and nucleic acids (see, e.g., WO 93/016383 for more discussion of indirect approaches to evaluate the electrical properties of a particle in an electrorotation system).

Advantageously, some embodiments are capable of measuring the electrical properties of a plurality of particles of various types, shapes, and sizes. For example, a biological sample may contain a heterogeneous population of particles. The methods and devices described herein can be used to identify homogeneous populations of moieties within a heterogeneous biological sample by classifying and grouping the various moieties according to their electrical properties. Accordingly, in certain embodiments, aliquots of a biological sample are placed in the devices described herein and electrorotation measurements are taken on the individual moieties. The data is compiled and moieties having similar electrical properties can be classified and grouped. That is, moieties that have similar electrical properties can be identified.

For some applications, for example, the ability to distinguish cells that produce a cellular substance from those that do not is desired. Cells that are actively producing a cellular substance (e.g., carbohydrate, lipid, peptide, nucleic acid, and the like) can exhibit different electrical properties than cells that are not actively producing the particular cellular substance. The methods and devices described herein can be used to rapidly screen a plurality of cells for their ability to produce a cellular substance. For example, cells can be transfected (e.g., at a low efficiency) to express a membrane protein, such as epidermal growth factor receptor (EGF receptor). Some population of the cells that undergo transfection will not express the membrane protein and some population will express the membrane protein. Thus, after transfection, a heterogeneous population of cells is obtained. The techniques described above can then be employed to identify a homogeneous population of cells within the heterogeneous population of transfectants.

In this illustrative, but non-limiting embodiment, antibodies to the expressed protein (e.g., EGF receptor) are generated or are obtained from a commercial supplier. These antibodies can then be attached to beads using the technique described above or by forming a covalent linkage through a hydroxy, carboxy or amino group and a reactive group on the carrier. Many kits for immobilizing antibodies to beads are commercially available (Pierce Chemical). The immobilized antibodies are then used to react with the heterogeneous population of cells. The cell/antibody/bead mixture is applied to the devices described herein and electrorotation measurements are taken on the beads before and after contact with the cells. The electrical properties of the beads that successfully bound to an EGF receptor expressing cell will be different than the electrical properties of the beads themselves. In this manner, a homogeneous population of cells that are producing a cellular substance are identified.

Of course, electrorotation measurements can be made directly on the membrane protein expressing cells and, in some cases, largely dependent on the protein expressed, differences in the electrical properties of cells actively producing the substance from cells not producing the substance can be measured. For example, cells that express proteins involved in ion transport would have electrical properties that are significantly different than cells that do not express these transport proteins and can be directly analyzed using the methods and devices described herein.

In addition to analyzing the electrical properties of various moieties, the the methods and devices described herein can be used to detect whether a reaction or interaction has occurred between, e.g., a cell or virus, or organelle and a molecule (e.g., antibody, peptide, chemical, or other cell). In one approach, for example, the electrorotation behavior of a cell or plurality of cells prior to exposure to a molecule of interest (referred to as a "binding partner" by virtue of the determined association with a particle or referred to as a "candidate binding partner" by virtue of the lack of certainty as to whether the molecule will associate with the particle) is determined. In certain embodiments various electrical properties are analyzed for these "control sample(s)". Next, a cell or plurality of cells is contacted with the binding partner, a sufficient time for interaction is provided, and the electrorotation behaviors of the exposed cell or plurality of cells are analyzed. In certain embodiments the identical parameters that were used to analyze the control sample(s) are used to analyze the exposed cell or plurality of cells. A comparative analysis can then be made between the control sample(s) and the exposed cell or plurality of cells and, from this information, the effect of the binding partner on the cell or plurality of cells can be determined. As described above, indirect measurement approaches can be used, as well.

In certain embodiments the electrorotation behaviors of individual cells prior to the exposure to the binding partner are measured and statistically analyzed. In certain embodiments the statistical analysis may comprise a simple average of the measured rotation rate for individual cells at various frequencies. Accordingly, the individual cells can be incubated with a candidate binding partner, the electrorotation behaviors are measured, and a statistical analysis is performed. The statistical data for the cells before and after incubation with the various candidate binding partners are then compared to see whether a significant change in cell's electrorotation properties has occurred.

By one approach, for example, a high-throughput electrorotation assay can be used to screen a chemical compound library for binding partners that modulate the electrical properties of cells. Accordingly, cells can be contacted with different chemical compounds ("candidate binding partners") from a compound library.

In certain embodiments the electrorotation behaviors of the cells are determined before and after the incubation of cells with the chemical compounds, however, control cells that were not contacted with the chemical can be used in the alternative. The electrorotation behavior for the cells is measured and population parameters are derived so as to determine whether a significant change in the parameters occurred following the incubation of the cells with the compounds. For example, if a chemical interacts with the cells, it may cause a biochemical reaction that will alter the biological properties of the cells, which will be detectable as a statistically significant change in an electrical property. Such changes in cell electrical properties can be detected by electrorotation measurements and the compounds that cause such changes can be identified as lead drug molecules. On the other hand, if a chemical compound does not interact with the cells, the cells will not exhibit a change in their electrorotation behavior.

In a simple case, the electrorotation behavior of the cells at a single characteristic frequency can be measured. As the name implies, the "characteristic frequency" is a frequency at which the electrorotation behavior of the cells strongly depends on the cell properties. The characteristic frequency can also be the frequency at which the cells, prior to exposure to the candidate binding partner, exhibits no or very little rotation. Thus, if the cells, after the incubation with a candidate binding partner, exhibit a strong no-zero rotation at this frequency, one can conclude that the cells have interacted with the binding partner. That is, if the interaction between the cells and the candidate binding partner has caused a change in cell electrorotation behaviors then one can conclude that the candidate binding partner is indeed a binding partner. On the other hand, if the average of rotation rates for individual cells after incubation with a candidate binding partner is also close to zero at this frequency, one may conclude that there is no change in cell electrorotation properties and the candidate binding partner does not interact with the cell.

Another method for determining whether the cells exhibit a statistically-significant change in cell properties before and after incubation with different types of assay molecules is to compare cell dielectric parameters. Accordingly, the measured electrorotation responses of individual cells are analyzed by performing mathematical fitting for the experimental rotation rates over the measured frequency range with a theoretical curve. The theoretical dependency of cell rotation rate on the frequency of the applied field is calculated using cell models and dielectric parameters in the model. The theoretical curves follow certain mathematical formulas (e.g. written analytical formula or the numerical relationships) with one or multiple parameters that may be varied to adjust the curve shapes. Thus, the fitting procedure may lead to one or multiple parameters in the model for each measured cell. These derived parameters can then be analyzed further using statistical methods to obtain population parameters and to compare these population parameters to determine whether statistically-significant changes occurred after the cells are incubated with a candidate binding partner.

Also contemplated here are methods that involve the quantitative analysis of the interaction between a plurality of cells and a binding partner (e.g., chemical, peptide, antibody, or other ligand). In some applications, for example, the methods and devices described herein can be used to determine the identity or concentration of a molecule in a biological sample. In other applications, it may be desired to determine the optimum concentration of a molecule that should be applied to cells. In this later application, the optimum concentration of a molecule to be added to a cell can be determined by evaluating the amount of binding partner needed to achieve a maximum electrorotation response.

These assays can be performed by using the approaches described above with slight modification. For example, the optimal amount of a compound to add a cell can be determined as follows. Various concentrations of binding partners are added to the cells in different reaction wells and then introduced into the devices described herein for determination of electrorotation properties. That is, a titration of binding partner is run on the electrorotation assay such that different concentrations of the binding partner are evaluated. The concentration of binding partner that leads to a maximum response can be identified.

In certain embodiments to determine the identity and concentration of a molecule in a biological sample, an indirect electrorotation analysis can be used. In certain embodiments this method can employ surface-activated microparticles, to which a detection agent is bound. The detection agent on microparticle surfaces (e.g., a dye, antigen, antibody, peptide, enzyme, nucleic acid, or other ligand) interacts with a molecule of interest in a biological sample. Multiple detection reagents that bind specifically to different microparticles and interact specifically with different target molecules can be used so that more than one target can be evaluated in the same assay.

In certain embodiments the electrorotation behaviors of the microparticles can be determined before contact with the biological sample. The biological sample is then added and a sufficient time for interaction is provided. After incubation, the electrorotation behaviors of the microparticles are measured. The measured values are then evaluated to determine whether a change in electrorotation behavior has occurred and to determine the magnitude of such change. The change in the cell rotation response will determine whether the biological sample contains molecules that interact with the coated microparticles. Furthermore, the change in the electrorotation response will correlate directly with the concentration of such molecules in the solution. By analyzing the changes in the electrorotation behaviors of the coated microparticles the composition and concentration of the molecule in the biological sample can be determined.

The foregoing applications are illustrative and not limiting. Using the teachings provided herein, numerous other application of the methods and devices described herein will be available to one of skill in the art.

EXAMPLES

The following examples are offered to illustrate, but not to limit the claimed invention.

Example 1

A High Throughput Electrorotation Flow Cytometer for Single-Cell Analysis in Continuous Flows In this study, we report a continuous flow based electrorotation mechanism called tunnel electrorotation (TROT) that can solve both the friction and the throughput issues encountered by prior works and realize a high throughput electrorotation based flow cytometer for label-free analysis of single cells.

Working Principle

DEP is a phenomenon in which a particle in a non-uniform electric field experiences an electrostatic force moving it towards a stronger electric field region if it is more polarizable than the medium (positive DEP or pDEP), or to a weaker electric field region if the particle is less polarizable than the medium (negative DEP, nDEP). To generate a DEP force on a particle, a spatial electric field intensity gradient is necessary. ROT is a phenomenon in which a particle rotates in a rotating electric field. The physical origin of ROT comes from the phase delay between the induced electric dipole on the particle and the external rotating field. This delay creates an angle between the induced dipole and the external field, and results in a mechanical torque on the particle for rotation. What determines the direction and the magnitude of the torque on a particle, in addition to the electric field strength and frequency, is the dielectric composition of the particles including its materials and structures. DEP and ROT have similar physical origins, both based on the interactions between the field-induced dipole on a particle and their relationship with the external field.

FIG. 1, panel (a), shows an illustrative schematic of a TROT device. The quadro-shaped electrodes along the entire channel provide a tunnel-shaped electric field distribution for tunable, sheathless, and three dimensional single-stream cell focusing in high-speed flows (Kung et al. (2016) *Small*, 12(32): 4343-4348). Electrodes on the top and bottom substrates are laid out and aligned with a straight microfluidic channel to provide negative DEP forces completely perpendicular to the hydrodynamic flow along the entire channel. Single-stream cell focusing is achieved by applying a combination of a.c. voltages ($A_1$, $A_2$, $A_3$, and $A_4$) with the same frequency ($\omega_1$) to the four corner electrodes to create an electric field minimum (the dark spot in FIG. 1, panel (b)) in the channel cross section (FIG. 1, panel (c)-i). Because cell focusing is achieved by negative DEP, randomly distributed cells in the inlet (FIG. 1, panel (a)-i)) migrate to the electric field minimum to achieve single-stream focusing.

To rotate the focused cells, a different set of electrical signals at a different frequency ($\omega_2$) is applied and superimposed on the electrodes. These signals have a 90-degree phase difference to their neighboring electrodes (FIG. 1, panel (c)-ii)). The rotation axis of cells is along the channel. The amplitude of rotation signals (B in FIG. 1, panel (c)-ii)) is usually smaller than the focusing signals ($A_1$, $A_2$, $A_3$, and $A_4$), and can be adjusted to control the cell rotation speed. FIG. 1, panel (b), shows the superimposed signal configuration on each electrode and the simulated electrical field distribution in the 80 μm×83 μm (width×height) channel cross section.

A high-speed camera can be utilized to capture images of rotating cells continuously. Post-processing and analysis of the captured images can give the information of size, texture, shape, and rotation speed of each individual cell.

The magnitude of DEP force on a spherical particle can be approximately expressed by the following equation derived based on the diploe approximation when a particle is exposed to an a.c. electric field [1].

$$\langle F_{DEP}(t) \rangle = \pi \varepsilon_m R^3 Re[CM^*(\omega)] \times \nabla(E^2) \qquad (1)$$

where $\langle F_{DEP}(t) \rangle$ refers to the time-average DEP force, $\varepsilon_m$ the permittivity of the medium surrounding the sphere, R the radius of the particle, ω the radian frequency of the applied electric field, and E is the magnitude of the imposed a.c. electric field. CM* is the frequency dependent Clausius-Mossotti factor given by $$CM^*(\omega) = \frac{\varepsilon_p^* - \varepsilon_m^*}{\varepsilon_p^* + 2\varepsilon_m^*} \qquad (2)$$

where $\omega_p^*$ and $\omega_m^*$ are the complex permittivities of the particle and the medium respectively, and $\varepsilon^* = \varepsilon - j\sigma/\omega$, where ε is the permittivity and σ is the conductivity. The magnitude of DEP force is linearly proportional to the gradient of the field strength and the volume of a particle. For a particle more polarizable than the medium, the real part of its CM* factor is bigger than zero, Re[CM*]>0, and it experiences a positive DEP force moving it toward the strong electric field region. On the other hand, if Re[CM*]<0, a particle experiences a negative DEP force moving it to the weak electric field region. DEP manipulation on mammalian cells is usually conducted in low ionic buffers for several reasons. One is that different types of mammalian cells suspended in low ionic buffers (0.01 S/m~0.1 S/m) show very distinct dielectric signatures and CM curves, which make cell and particle sorting easier to perform. Second, higher voltage can be applied to electrodes to generate larger DEP forces on cells without inducing electrolysis on electrodes or causing significant heating.

On the other hand, under a rotating electric field, a spherical dielectric particle is subjected to a torque, which is defined as $$\langle T_{ROT}(t) \rangle = 4\pi \varepsilon_m R^3 Im[CM^*(\omega)] \times E^2 \qquad (3)$$

where Im[CM*] stands for the imaginary part of the Clausius-Mossotti factor, and E is the electric field magnitude.

If the constant angular velocity (Ω) of a particle is assumed, then the hydrodynamic torque $T_f$ arising from the Stokes drag force is given by $$T_f = 8\pi \eta \Omega R^3 \qquad (4)$$

where η is the viscosity of the medium, and R is the radius of the particle.

In equilibrium, $|T_{ROT}|=|T_f|$. Using equation (3) and (4) we then have $$\Omega = \frac{\varepsilon_m}{(2\eta)} Im[CM^*(\omega)] \times E^2 \qquad (5)$$

Equation (2), along with equation (5), indicates that the particle's steady angular speed is dependent on the medium and the particle's electrical properties, the electric field magnitude.

Device Fabrication

FIG. 2 shows a schematic of the microfabrication process flow of a TROT device (see also Kung et al. (2015) *Lab on a Chip*, 15(8): 1861-1868).

Step 1: It starts from fabricating a SU-8 mold master on a silicon wafer using photolithography (FIG. 2, panel (a)). The master needs to be surface treated with trichloro (1H, 1H,2H,2H-perfluorooctyl) silane (97%, Sigma-Aldrich, USA), also called PFOCTS, to facilitate later demolding.

Step 2: This is to fabricate a hybrid stamp. It starts from preparing the Sylgard 184 silicone elastomer mixture (Dow Corning Corporation, Miland, USA). The weight ratio of Base:Curing agent is 10:1. Few drops of this mixture are poured into a petri dish. A suitable size of polystyrene plastic plate is cut and pressed against the bottom of the petri dish under a pressure of 3 psi. A thin layer of polydimethylsiloxane (PDMS) with a thickness of roughly 30 μm is formed between the petri dish and the plastic plate. Additional uncured PDMS is poured to fill up the petri dish, and followed by a curing step at 60° C. in an oven for 12 hours. A hybrid stamp is formed when the plastic plate together with a thin PDMS layer on its surface is peeled off from the petri dish (FIG. 2, panel (b)). The hybrid stamp is also surface treated with PFOCTS for 6 hours.

Step 3: To fabricate a PDMS thin film with through-layer structures, uncured PDMS is poured onto the SU-8 master mold, pressed by the hybrid stamp under a pressure of 4 psi, and cured at 50° C. in an oven for an hour. Demolding PDMS films from the master mold. During the demolding process, the cured PDMS thin film has stronger adhesion to the hybrid stamp than the master mold since more PFOCTS is coated on the master mold due to a longer treatment time (FIG. 2, panel (c)).

Step 4: To transfer the PDMS thin film, oxygen plasma treatment is performed on both the PDMS thin film on the hybrid stamp and the substrate with strip electrodes to be bonded. The alignment between the channel and strip electrodes is needed (FIG. 2, panel (d)).

Step 5 & 6: To remove the hybrid stamp, it starts from peeling off the bulk PDMS part on the plastic plate (FIG. 2, panel (e)), and then dissolving the polystyrene plastic plate in an acetone bath for 4 hours (FIG. 2, panel (f)).

Step 7: After step 6, which leaves a thin residual PDMS film on the substrate that can be easily peeled off from the device due to prior PFOCTS treatment (FIG. 2, panel (g)) to finish the transfer. This mechanically gentle releasing technique allows us to transfer PDMS thin film with fragile substrates, such as a high aspect ratio vertical wall.

Step 8: Finally, a top coverslip with strip electrodes are aligned and bonded to form a heterogeneously integrated 3D microfluidic TROT device (FIG. 2, panel (h)).

Experimental Results

Figure 3:
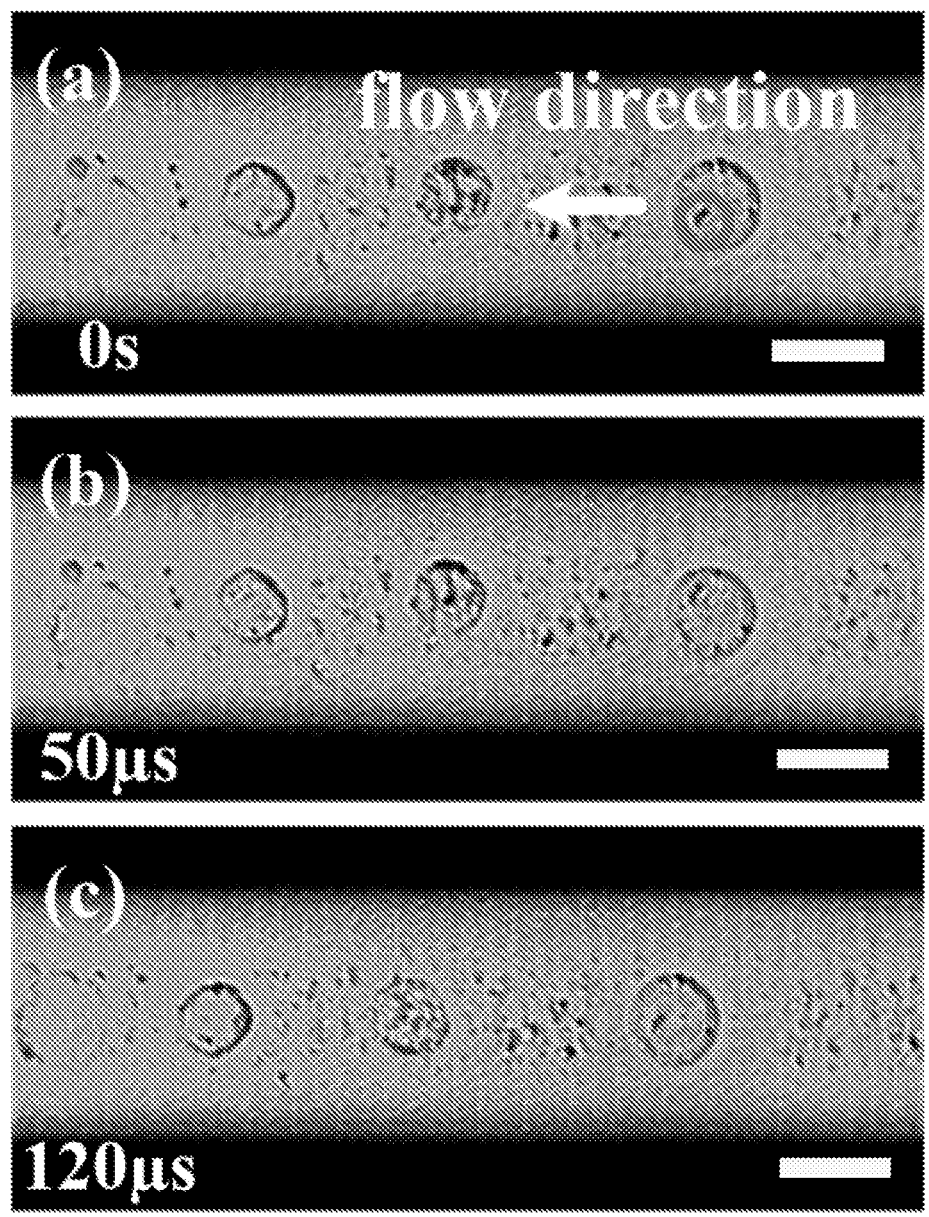
FIG. 3, panels a-c, shows time-lapsed microscopy images of THP1 cells flowing at a speed of 2.1 cm/s. The cell focusing signal is 24 Vpp at 20 kHz. The rotation signal is 20 Vpp at 60 kHz. The images were captured at 10000 fps. In order to trace the axial rotation movement, a surface marker on the cell membrane (red encircled spot) in panel (a) is used to facilitate the visualization. The scale bar is 30 μm.

FIG. 3 shows the time-lapsed microscope images of THP1 cells flowing in a TROT channel at a speed of 2.1 cm/s. Cells were suspended in an isotonic buffer with a conductivity of 0.01 S/m. The cell focusing signal is $24V_{pp}$ at 20 kHz. The rotation signal is $20V_{pp}$ at 60 kHz. In order to trace the axial rotation movement, a surface marker on the cell membrane (red encircled spot) in FIG. 3, panel (a) is used to facilitate the visualization. The images were captured at 10000 fps. As been shown, cells are focused and rotated simultaneously in a continuous flow, which demonstrates the capability of this TROT platform.

Figure 4:
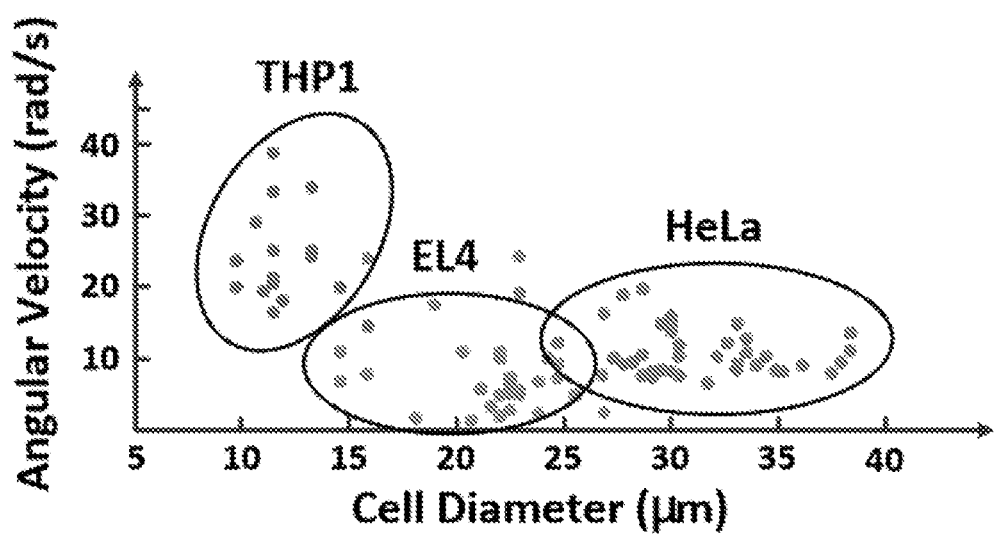
FIG. 4 shows a size v.s. rotation rate distribution plot of three different cell types, THP1, EL4, and GFP-HeLa cells. The rotation rate of each cell is calculated by analyzing the captured images. The input flow rate is 0.15 ml/h and the cell concentration is 106 cells/ml. This corresponds to a throughput of 42 cells/sec.

FIG. 4 shows the size v.s. rotation rate distribution plot of three different cell types, THP1, EL4, and GFP-HeLa cells. The rotation rate of each cell is calculated by analyzing the captured images. The input flow rate is 0.15 ml/h and the cell concentration is $10^6$ cells/ml. This corresponds to a throughput of 42 cells/sec. Compared to prior batch-mode electrorotation devices in which single cells need to be preloaded into individual cages, rinsed after measurement, and reloaded for next run measurement, a time consuming process that may takes tens of minutes to finish, TROT provides a 4 orders of magnitude higher throughput than prior ROT devices.

CONCLUSION

In this work, we report a novel microfluidic-based high-throughput electrorotation flow cytometer, called TROT, for label-free single-cell analysis in continuous flows. This is realized by a single microfluidic channel with electrodes for high precision 3D single stream focusing and rotation of cells simultaneously and continuously in high speed flows. This device provides a 4 orders of magnitude higher throughput than prior electrorotation based cytometers.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for electrorotation flow cytometry, said device comprising:
    a microfluidic channel comprising a plurality of electrodes disposed to provide dielectrophoretic (DEP) forces that are perpendicular to hydrodynamic flow along the channel; and
    a fluid within said channel providing said hydrodynamic flow along said channel;
    wherein said device is configured to apply focusing voltages to said electrodes that provide an electric field minimum in said channel and that focus cells, particles, and/or molecules or molecular complexes within said channel; and
    wherein said device is configured to apply rotation-inducing voltages to said electrodes where said rotation-inducing voltages have phase differences that induce rotation of said cells, particles, molecules and/or molecular complexes as they flow through said channel.

2. The device of claim 1, wherein said device comprises two pairs of electrodes disposed parallel to each other around the microfluidic channel.

3. The device of claim 1, wherein:
    said plurality of electrodes comprises electrodes disposed along each side of said microfluidic channel at or near the top of said channel and electrodes disposed along each side of said microfluidic channel at or near the bottom of said channel; or said plurality of electrodes comprises electrodes disposed along the midline of each side of said microfluidic channel and along the midline of the top and bottom of said channel.

4. The device of claim 1, wherein device is configured to produce focusing voltages that produce negative DEP forces perpendicular to said hydrodynamic flow along said channel.

5. The device of claim 1, wherein said focusing voltages are ac voltages all having the same frequency.

6. The device of claim 1, wherein device is configured to apply said rotation-inducing voltages so that neighboring electrodes have a 90 degree phase difference and diagonally opposed electrodes have the same phase.

7. The device of claim 1, wherein said rotation-inducing voltages are ac voltages and wherein:
said rotation-inducing voltages are at a frequency that is different than the frequency of said focusing voltages; and/or
said rotation-inducing voltages have an amplitude that is smaller than the amplitude of the focusing voltages.

8. The device of claim 1, wherein:
said focusing voltages and said rotation-inducing voltages are provided in the same region of said microfluidic channel; or
said focusing voltages and said rotation-inducing voltages are provided in different regions of said microfluidic channel.

9. The device of claim 1, wherein:
said focusing voltages are independently at a frequency ranging from about 15 kHz to about 25 kHz, and/or about 20 kHz; and/or
said focusing voltages have amplitudes that independently range from about 20 Vpp to about 30 Vpp, and/or are about 24 Vpp; and/or
said rotation-inducing voltages are independently at a frequency ranging from about 50 kHz to about 70 kHz, and/or are about 60 kHz; and/or
said rotation inducing voltages independently have amplitudes that range from about 10 Vpp to about 30 Vpp, and/or are about 20 Vpp.

10. The device of claim 1, wherein:
said focusing voltages provide a field minimum at the center of said microfluidic channel; or
said focusing voltages provide a field minimum at or near one side of said channel; or
said focusing voltages provide a field minimum at or near a lower or upper corner (diagonal region) of said channel.

11. The device of claim 1, wherein:
said microfluidic channel has an average depth that ranges from about 50 μm up to about 200 μm; and
said microfluidic channel has an average width that ranges from about 30 μm to about 200 μm.

12. The device of claim 11, wherein said microfluidic channel that has a cross-section that is about 80 μm×83 μm (width×height).

13. The device of claim 1, wherein:
said fluid is a buffer; and/or
said fluid has a conductivity ranging from about 0.005 S/m up to about 2.0 S/m; and/or
said fluid has a conductivity of about 0.01 S/m; and/or
said fluid comprises a mammalian ringer's solution; and/or
said fluid comprises PBS.

14. The device of claim 1, wherein said channel is fabricated from an elastomeric material selected from the group consisting of polydimethylsiloxane (PDMS), polyolefin plastomers (POPs), perfluoropolyethylene (a-PFPE), polyurethane, polyimides, and cross-linked NOVOLAC® (phenol formaldehyde polymer) resin.

15. The device of claim 1, wherein said device further comprises a camera configured to capture images of said cells, particles and/or molecules or molecular complexes as they flow through said channel.

16. A method of inducing rotation of a plurality of cells, particles, molecules and/or molecular complexes, said method comprising:
introducing said cells, particles, molecules and/or molecular complexes into a device of claim 1;
operating said device to provide said focusing voltages to focus said cells, particles, molecules and/or molecular complexes within said channel; and
operating said device to provide said rotation-inducing voltages to induce rotation of said cells, particles, molecules and/or molecular complexes as they flow through said microfluidic channel.

17. A method of determining an electrical property of cells, particles, molecules and/or molecular complexes, said method comprising:
introducing at least one of said cells, particles, molecules and/or molecular complexes into a device of claim 1;
operating said device to provide said focusing voltages to focus said cells, particles, molecules and/or molecular complexes within said channel;
operating said device to provide said rotation-inducing voltages to induce rotation of said cells, particles, molecules and/or molecular complexes as they flow through said microfluidic channel; and
measuring the rotation of said at least one of said cell, particle, molecule and/or molecular complex and thereby determining the electrical property of said cell, particle, molecule and/or molecular complex.

18. A method of identifying an agent that changes the electrorotational properties of a cell, said method comprising:
introducing cells into a device according of claim 1;
operating said device to provide said focusing voltages to focus said cells within said channel;
operating said device to provide said rotation-inducing voltages to induce rotation of said cells as they flow through said microfluidic channel;
measuring the rotation of said cells;
contacting said cells with a test agent;
operating said device to provide said focusing voltages to focus cells contacted with said test agent within said channel;
operating said device to provide said rotation-inducing voltages to induce rotation of said cells contacted with said test agent as they flow through said microfluidic channel;
comparing the rotation of a cell that was not exposed to said candidate molecule with the rotation of said cell after contact with said candidate molecule; and
identifying said candidate molecule as an agent that changes said electrorotational properties of said cell if said cells contacted with said candidate molecule have different electrorotational properties than said cells not contacted with said test agent.

19. A method of determining the identity or concentration of an analyte in a sample comprising, said method comprising:
introducing said sample into a device of claim 1;

introducing particles attached to a detection reagent that binds to said analyte into said device;

operating said device to provide said focusing voltages to focus said particles within said channel;

operating said device to provide said rotation-inducing voltages to induce rotation of said particles as they flow through said microfluidic channel; and determining the identity or concentration of said molecule in said biological sample by comparing the rotation of said particles contacted with said biological sample with particles that have not been contacted with said biological sample where the difference in rotation of the particles contacted with the sample and the particles not contacted with the sample provides a measure of the identity or concentration of said analyte in said sample.

* * * * *